(12) United States Patent
Tchertkov et al.

(10) Patent No.: US 10,667,705 B2
(45) Date of Patent: Jun. 2, 2020

(54) SYSTEM AND METHOD FOR OBTAINING BLOOD PRESSURE MEASUREMENT

(71) Applicant: QUALCOMM Incorporated, San Diego, CA (US)

(72) Inventors: Igor Tchertkov, San Jose, CA (US); Evgeni Yurij Poliakov, San Mateo, CA (US); Russell Wayne Gruhlke, Milpitas, CA (US); Russel Allyn Martin, Menlo Park, CA (US); Evgeni Petrovich Gousev, Saratoga, CA (US); Muhammed Ibrahim Sezan, Los Gatos, CA (US)

(73) Assignee: QUALCOMM Incorporated, San Diego, CA (US)

( * ) Notice: Subject to any disclaimer, the term of this patent is extended or adjusted under 35 U.S.C. 154(b) by 773 days.

(21) Appl. No.: 14/863,352

(22) Filed: Sep. 23, 2015

(65) Prior Publication Data
US 2017/0079534 A1    Mar. 23, 2017

(51) Int. Cl.
*A61B 5/026* (2006.01)
*A61B 5/021* (2006.01)
(Continued)

(52) U.S. Cl.
CPC ........ *A61B 5/02427* (2013.01); *A61B 5/0261* (2013.01); *A61B 5/02125* (2013.01);
(Continued)

(58) Field of Classification Search
CPC . A61B 5/0075; A61B 5/0084; A61B 5/02125; A61B 5/02427; A61B 5/681;
(Continued)

(56) References Cited

U.S. PATENT DOCUMENTS

| 5,790,729 A | * | 8/1998 | Pologe | .................. G02B 6/125 |
| | | | | 385/20 |
| 5,964,701 A | | 10/1999 | Asada et al. | |

(Continued)

FOREIGN PATENT DOCUMENTS

| CN | 104411241 A | 3/2015 |
| CN | 104586407 A | 5/2015 |

(Continued)

OTHER PUBLICATIONS

International Search Report and Written Opinion—PCT/US2016/046207—ISA/EPO—dated Nov. 9, 2016.

*Primary Examiner* — Gary Jackson
*Assistant Examiner* — Pamela M. Bays
(74) *Attorney, Agent, or Firm* — Kilpatrick Townsend & Stockton, LLP/QUALCOMM Incorporated

(57) ABSTRACT

Methods, systems, computer-readable media, and apparatuses for obtaining blood pressure measurements are presented. The blood pressure measurements may be obtained by determining a pulse-transit time (PTT) as a function of a photoplethysmography (PPG) measurement and electrocardiogram (ECG) measurement. A mobile device includes outer body sized to be portable for a user of the mobile device. The mobile device also includes a plurality of light emitting components distributed along at least one portion of the mobile device and a plurality of light collecting components configured to measure reflected light from the plurality of light emitting components reflected off of blood vessels within the user. The light emitting and light collecting components are distributed along the at least one portion of the mobile device. The mobile device may also include a light guide configured to direct light emitted by the at least one light emitting component toward blood vessels with the user.

30 Claims, 12 Drawing Sheets

(51) Int. Cl.
*A61B 5/0402* (2006.01)
*A61B 5/00* (2006.01)
*A61B 5/024* (2006.01)

(52) U.S. Cl.
CPC .......... *A61B 5/02416* (2013.01); *A61B 5/681* (2013.01); *A61B 5/6826* (2013.01); *A61B 5/0075* (2013.01); *A61B 5/0084* (2013.01); *A61B 5/0402* (2013.01); *A61B 2562/04* (2013.01)

(58) Field of Classification Search
CPC ... A61B 5/6826; A61B 5/7255; A61B 5/0261; A61B 5/0295
See application file for complete search history.

(56) References Cited

U.S. PATENT DOCUMENTS

| | | | |
|---|---|---|---|
| 8,934,952 B2 | 1/2015 | Leboeuf et al. | |
| 8,956,303 B2 | 2/2015 | Hong et al. | |
| 2006/0072203 A1* | 4/2006 | Lee | G02B 5/045 359/625 |
| 2006/0122520 A1* | 6/2006 | Banet | A61B 5/021 600/503 |
| 2010/0113902 A1 | 5/2010 | Hete et al. | |
| 2011/0004106 A1* | 1/2011 | Iwamiya | A61B 5/0059 600/476 |
| 2011/0118574 A1 | 5/2011 | Chang et al. | |
| 2012/0179011 A1 | 7/2012 | Moon et al. | |
| 2013/0006074 A1 | 1/2013 | Pologe | |
| 2013/0131519 A1* | 5/2013 | LeBoeuf | A61B 5/0077 600/476 |
| 2013/0310669 A1 | 11/2013 | Nitzan | |
| 2014/0183342 A1* | 7/2014 | Shedletsky | G06F 1/1637 250/215 |
| 2015/0018647 A1 | 1/2015 | Mandel et al. | |
| 2015/0164352 A1* | 6/2015 | Yoon | A61B 5/7221 600/301 |
| 2017/0079535 A1 | 3/2017 | Tchertkov et al. | |

FOREIGN PATENT DOCUMENTS

| | | |
|---|---|---|
| WO | WO-2014089665 A1 | 6/2014 |
| WO | WO-2014168718 A1 | 10/2014 |
| WO | 2015001434 A1 | 1/2015 |

* cited by examiner

SYSTEM AND METHOD FOR OBTAINING BLOOD PRESSURE MEASUREMENT

BACKGROUND

Aspects of the disclosure relate to mobile devices, and more particularly, a system and method for obtaining at least one bodily function measurement of a user operating a mobile device.

It is often desirable for a user to be aware his/her bodily function measurements. Recently, many individuals wear small portable devices capable of measuring their heart rate (HR) and other physiological information. One of the most popular techniques used by these devices to measure heart rate is photoplethysmography (PPG). The PPG method works well when heart rate is measured on an individual's finger. However, many of the small portable fitness devices are wearable electronics that are typically package in the form of a watch (e.g., smart watch), activity monitoring band (e.g., worn on the wrist), etc. However, the vasculature of the human wrist is such that the PPG signal measured at the wrist at least an order of magnitude weaker than when measured at the finger. Additionally, current wrist worn devices are subject to motion artifacts, further exacerbating this issue.

Motion artifacts can be caused by a variety of mechanisms. An example of such a mechanism is a small uncontrollable motion of human body components (e.g., muscle, bone, ligament, blood vessel, etc.) associated with the acts of living, such as breathing. Another example is blood "sloshing" in the blood vessels caused by motion of an individual's arm with varying acceleration, such as swinging arms when walking. Yet another example is the relative motion of the PPG sensor itself and blood-perfused tissue. Such mechanisms can dwarf the "useful" modulation of the PPG signal caused by the true heart beating. It is very challenging to separate the individual's actual HR from the modulation of the optical signal caused by the motion artifacts.

Accordingly, a need exists for a wearable heart rate PPG sensor that is immune to motion artifacts.

BRIEF SUMMARY

Certain implementations are described for obtaining at least one bodily function measurement of a user operating a mobile device.

In some implementations, a mobile device for obtaining a photoplethysmography (PPG) measurement, includes an outer body sized to be portable for a user of the mobile device. The mobile device also includes a plurality of light emitting components distributed along at least one portion of the mobile device. The mobile device further includes a plurality of light collecting components configured to measure reflected light from the plurality of light emitting components reflected off of blood vessels within the user, wherein the plurality of light collecting components are distributed along the at least one portion of the mobile device, and wherein a processor is configured to obtain the PPG measurement based on the reflected light measured by the plurality of light collecting components.

In some implementations, the plurality of light emitting components comprises at least three light emitting components.

In some implementations, the at least one portion is a 360 degree circumference.

In some implementations, the processor is further configured to average the reflected light measurement from each of the plurality of light collecting components.

In some implementations, the plurality of light emitting components distributed along the at least one portion of the mobile device are distributed in an axially symmetrical arrangement.

In some implementations, the processor is further configured to determine a blood pressure (BP) measurement of the user based at least in part on the obtained PPG measurement.

In some implementations, the mobile device is at least one of a watch, ring, or bracelet.

In some implementations, the plurality of light emitting components comprise light emitting diodes (LEDs) and the plurality of light collecting components comprise photodiodes.

In some implementations, a method for obtaining a photoplethysmography (PPG) measurement includes measuring, via a plurality of light collecting components, reflected light from a plurality of light emitting components reflected off of blood vessels within a user of a mobile device, wherein the plurality of light emitting components are distributed along at least one portion of the mobile device, and wherein the mobile device comprises an outer body sized to be portable for the user. The method also includes obtaining the PPG measurement based on the reflected light measured by the plurality of light collecting components, wherein the plurality of light collecting components are distributed along the at least one portion of the mobile device.

In some implementations, an apparatus for obtaining a photoplethysmography (PPG) measurement includes means for measuring, via a plurality of light collecting components, reflected light from a plurality of light emitting components reflected off of blood vessels within a user of a mobile device, wherein the plurality of light emitting components are distributed along at least one portion of the mobile device, and wherein the mobile device comprises an outer body sized to be portable for the user. In some implementations, the apparatus also includes means for obtaining the PPG measurement based on the reflected light measured by the plurality of light collecting components, wherein the plurality of light collecting components are distributed along the at least one portion of the mobile device.

In some implementations, one or more non-transitory computer-readable media storing computer-executable instructions for obtaining a photoplethysmography (PPG) measurement that, when executed, cause one or more computing devices included in a mobile device to measure, via a plurality of light collecting components, reflected light from a plurality of light emitting components reflected off of blood vessels within a user of a mobile device, wherein the plurality of light emitting components are distributed along at least one portion of the mobile device, and wherein the mobile device comprises an outer body sized to be portable for the user. In some implementations the instructions, when executed, further cause the one or more computing devices to obtain the PPG measurement based on the reflected light measured by the plurality of light collecting components, wherein the plurality of light collecting components are distributed along the at least one portion of the mobile device.

In some implementations, a mobile device for obtaining a photoplethysmography (PPG) measurement includes an outer body sized to be portable for a user of the mobile device. In some implementations, at least one light emitting component coupled to a light guide, the light guide configured to direct light emitted by the at least one light emitting component toward blood vessels with the user. In some implementations, at least one light collecting component coupled to the light guide, wherein the at least one light emitting component is configured to measure reflected light from the at least one light emitting component reflected off of blood vessels within the user, and wherein a processor is configured to obtain the PPG measurement based on the reflected light measured by the at least one light collecting component.

In some implementations, the light guide comprises a turning film operable to change a direction of the light emitted by the at least one light emitting component.

In some implementations, the outer body comprises a 360 degree circumference.

In some implementations, the light guide encompasses the 360 degree circumference.

In some implementations, the processor is further configured to determine a blood pressure (BP) measurement of the user based at least in part on the obtained PPG measurement.

In some implementations, the mobile device is at least one of a watch, ring, or bracelet.

In some implementations, the at least one light emitting component comprises a light emitting diode (LED) and the at least one light collecting component comprises a photodiode.

In some implementations, a method for obtaining a photoplethysmography (PPG) measurement includes measuring, via at least one light collecting component coupled to a light guide, reflected light from at least one light emitting component reflected off of blood vessels within a user of a mobile device, wherein the at least one light emitting component is coupled to the light guide, wherein the light guide is configured to direct light emitted by the at least one light emitting component toward blood vessels within the user, and wherein the mobile device comprises an outer body sized to be portable for the user. The method also includes obtaining the PPG measurement based on the reflected light measured by the at least one light collecting component.

In some implementations, an apparatus for obtaining a photoplethysmography (PPG) measurement includes means for measuring, via at least one light collecting component coupled to a light guide, reflected light from at least one light emitting component reflected off of blood vessels within a user of a mobile device, wherein the at least one light emitting component is coupled to the light guide, wherein the light guide is configured to direct light emitted by the at least one light emitting component toward blood vessels within the user, and wherein the mobile device comprises an outer body sized to be portable for the user. The apparatus also includes means for obtaining the PPG measurement based on the reflected light measured by the at least one light collecting component.

In some implementations, one or more non-transitory computer-readable media storing computer-executable instructions for obtaining a photoplethysmography (PPG) measurement that, when executed, cause one or more computing devices included in a mobile device to measure, via at least one light collecting component coupled to a light guide, reflected light from at least one light emitting component reflected off of blood vessels within a user of a mobile device, wherein the at least one light emitting component is coupled to the light guide, wherein the light guide is configured to direct light emitted by the at least one light emitting component toward blood vessels within the user, and wherein the mobile device comprises an outer body sized to be portable for the user. In some implementations the instructions, when executed, further cause the one or more computing devices to obtain the PPG measurement based on the reflected light measured by the at least one light collecting component.

BRIEF DESCRIPTION OF THE DRAWINGS

Aspects of the disclosure are illustrated by way of example. In the accompanying figures, like reference numbers indicate similar elements, and.

DETAILED DESCRIPTION

Figure 1:
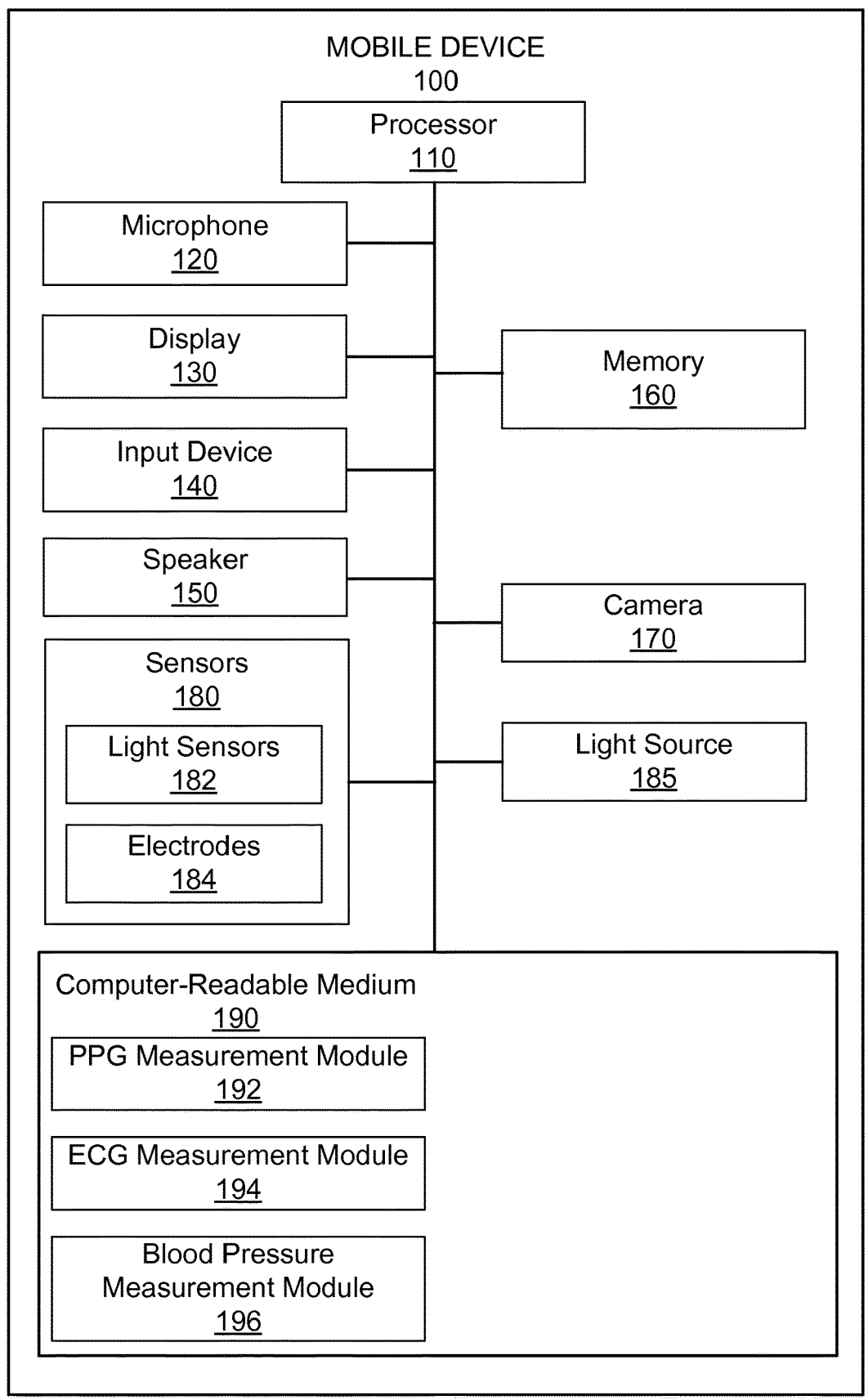
FIG. 1 illustrates a simplified block diagram of a mobile device that may incorporate one or more implementations.

Several illustrative implementations will now be described with respect to the accompanying drawings, which form a part hereof. While particular implementations, in which one or more aspects of the disclosure may be implemented, are described below, other implementations may be used and various modifications may be made without departing from the scope of the disclosure or the spirit of the appended claims.

As described above, many existing portable devices capable of measuring HR are susceptible to providing inaccurate data due to motion artifacts. For example, when a user in engaged in a physical activity such as typing, gesturing, walking, running, etc., the magnitude of the PPG signal caused by these motion artifacts simply dwarf the "useful" modulation of the PPG signal caused by the user's actual heartbeat. Additionally, motion artifacts can be caused by the inertial motion of blood. Blood has a mass and thus responds to swinging arm motions by "sloshing" in the blood vessels and blood-perfused tissue that is in sync with the arm swinging. Lastly, motion artifacts may also result from the relative motion of the PPG sensor and blood-perfused tissue. For example, a small portable device can hold the PPG sensor in close/tight contact with the user's skin. However, wearing the device too tight on the wrist (or other body part) is often uncomfortable and users prefer a looser fit. The device, having its own mass, may respond to the user's hand swinging by moving normal to the user's skin and also tangentially to the user's skin. Both types of motion, however, can modulate the HR signal in a period fashion, giving rise to motion artifacts.

As illustrated, the currently existing PPG sensors are prone to motion artifacts. It is quite challenging for the existing solutions to separate a user's actual HR from modulation of the optical signal caused by motion artifacts. This is especially true when the motion artifacts are period in nature and their frequency is close to the HR frequency. In this circumstance, the separation of the motion artifact signal portion from the actual HR signal portion is the most challenging. The weakness of the PPG signal generated on the wrist only exacerbates this difficulty.

Some Implementations pertain to a PPG sensor geometries capable of making more accurate and robust HR measurements when worn on a body part with a quasi-axi-symmetrical shape (e.g., wrist, finger, ankle, neck, etc.). The wearable system may not need to have an accelerometer or sophisticated software algorithms to remove motion artifacts. Further, the wearable system can operate on lower power and have a shorter bill of materials (BOM) than existing solutions.

The wearable system can include two or more light sources that are arrange in an axi-symmetrical configuration within a cylindrical housing. The light sources may wrap around a user extremity within the cylindrical housing. Because the light sources are uniform around the housing, the accuracy of the device in measuring PPG may not be hindered by motion artifacts because the same blood flow would still be interpreted even if the device were rotated or moved by typical user motion. Additionally, the cylindrical housing may include optical components with turning features that can scatter the reflection of the light transmitted by the light source throughout the cylindrical shape of the device.

Blood Pressure Measurement Device

FIG. 1 illustrates a simplified block diagram of a mobile device 100 that may incorporate one or more implementations. Mobile device 100 may include a processor 110, microphone 120, display 130, input device 140, speaker 150, memory 160, camera 170, sensors 180, light source 185, and computer-readable medium 190.

Processor 110 may be any general-purpose processor operable to carry out instructions on the mobile device 100. The processor 110 is coupled to other units of the mobile device 100 including microphone 120, display 130, input device 140, speaker 150, memory 160, camera 170, sensors 180, light source 185, and computer-readable medium 190.

Microphone 120 may be any an acoustic-to-electric transducer or sensor that converts sound into an electrical signal. The microphone 120 may provide functionality for a user of the mobile device 100 to record audio or issue voice commands for the mobile device 100.

Display 130 may be any device that displays information to a user. Examples may include an LCD screen, CRT monitor, or seven-segment display.

Input device 140 may be any device that accepts input from a user. Examples may include a keyboard, keypad, or mouse. In some implementations, the microphone 120 may also function as an input device 140.

Speaker 150 may be any device that outputs sound to a user. Examples may include a built-in speaker or any other device that produces sound in response to an electrical audio signal and/or ultrasonic signal(s).

Memory 160 may be any magnetic, electronic, or optical memory. It can be appreciated that memory 160 may include any number of memory modules. An example of memory 160 may be dynamic random access memory (DRAM).

Camera 170 is configured to capture one or more images via a lens located on the body of mobile device 100. The captured images may be still images or video images. The camera 170 may include a CMOS image sensor to capture the images. Various applications running on processor 110 may have access to camera 170 to capture images. It can be appreciated that camera 170 can continuously capture images without the images actually being stored within the mobile device 100. Captured images may also be referred to as image frames.

Sensors 180 may be a plurality of sensors configured to obtain data accessible by the processor. The sensors 180 may also be physically coupled to the outer body of the mobile device 100. The plurality of sensors 180 may include one or more light sensors 182 and/or one or more electrodes 184. The light sensors 182 may be configured to facilitate measurement of reflected light from the light source 185 (described below) reflected off of blood vessels within a user of the mobile device 100 to obtain the a PPG measurement indicative of the user's blood volume. Light sensors 182 may be referred to as light collecting components. A portion of a user of the mobile device's 100 body may complete a circuit between a first electrode and a second electrode, e.g., when the user touches both electrodes 184. The electrodes 184 may be configured to facilitate measurement of heart electrical activity of the user to obtain an ECG measurement.

Light source 185 may be any source of light configured to emit light through a user's body. In some implementations, the light source 185 may be a LED light source, a vertical cavity surface emitting laser (VCSEL), or any other type of light source. The emitted light may be of a wavelength that can pass through parts of a user's body. For example, the light source 185 may emit LED light through a user's wrist. In some implementations, the mobile device 100 may include multiple light sources 185. The light emitted from light source 185 may reflect off of blood vessels within the user's body and the reflected light may be measured by one or more light sensors 182 to obtain a PPG measurement, as described above. It can be appreciated that emitted light may be of different wavelengths depending on different wavelengths. For example, different wavelengths of light may be appropriate to improve the signal, reduce noise, deal with dark skin colors, measure the blood's oxygen content, or penetrate to different depths of the user's body. In some implementations, the light source 185 may be continuous or the light source 185 may be made up of a number of discrete light sources. Light source 185 may include one or more light sources. Light source 185 may also be referred to as a light emitting component.

Computer-readable medium 190 may be any magnetic, electronic, optical, or other computer-readable storage medium. Computer-readable medium 190 includes PPG measurement module 192, ECG measurement module 194, and blood pressure measurement module 196.

PPG measurement module 192 is configured to, when executed by processor 110, obtain a photoplethysmography (PPG) measurement. The PPG measurement may be a measurement of blood volume of a user operating the mobile device 100. The PPG measurement may be obtained by the PPG measurement module 192 in response to a user action. The PPG measurement module 192 may interface with the light source 185 and light sensors 182 in order to obtain the PPG measurement. Upon indication by the user of a need for a PPG measurement, the PPG measurement module 192 may direct the light source 185, or multiple light sources, to emit light through the user's body. As described above, the emitted light may reflect off or transmitted through blood vessels within the user's body and may be detected by one or more light sensors 182 within the mobile device 100. The PPG measurement module 192 may measure, by interfacing with the one or more light sensors, the amount of reflected or transmitted light detected by the one or more light sensors 182. The PPG measurement module 192 may then determine a PPG measurement that is indicative of the user's blood volume based on the measurement of the reflected light.

ECG measurement module 194 is configured to, when executed by processor 110, obtain an electrocardiography (ECG) measurement. The ECG measurement may be a measurement of heart electrical activity of a user operating the mobile device 100. The ECG measurement may be obtained by the ECG measurement module 194 in response to a user action. The ECG measurement module 194 may interface with the electrodes 184 in order to obtain the ECG measurement. Upon indication by the user of a need for an ECG measurement, the ECG measurement module 194 may interface with the electrodes 184 to measure (assuming the user's body completes a circuit between the electrodes 184) electrical impulse(s) generated by the polarization and depolarization of cardiac tissue within the user's body. In some implementations, the electrical impulse(s) may be generated by the beating of the user's heart. In some implementations, the ECG measurement module 194 may interface with the electrodes 184 to measure the electrical impulse(s) automatically upon the user's body completing a circuit between the electrodes 184. The ECG measurement module 194 may then determine an ECG measurement based on the measured electrical impulse(s). It can be appreciated that ECG measurement can be obtained using two or more electrode leads.

Blood pressure measurement module 196 is configured to, when executed by processor 110, generate a blood pressure measurement of the user based on the PPG measurement and the ECG measurement. According to Poon, C. C. Y.; Zhang, Y. T. "Cuff-less and Noninvasive Measurements of Arterial Blood Pressure by Pulse Transit Time", *Engineering in Medicine and Biology 27th Annual Conference*, 2005. *IEEE*, On page(s): 1-4, the calculation of the blood pressure measurement based on the PPG measurement and the ECG measurement is well known in the art.

It can be appreciated that the outer body of the mobile device 100 may be sized to be portable for a user. It can be appreciated that the term "portable" may refer to something that is able to be easily carried or moved, and may be a light and/or small. In some implementations, the term portable may refer to something easily transportable by the user or wearable by the user. For example, the mobile device 100 may be a smartphone device or a watch wearable by the user. Other examples of portable devices include a head-mounted display, calculator, portable media player, digital camera, pager, personal navigation device, etc. Examples of devices that may not be considered portable include a desktop computer, traditional telephone, television, appliances, etc. It can be appreciated that the bodily function measurements can be obtained via the smartphone, watch, or any other of the mentioned devices.

Figure 2:
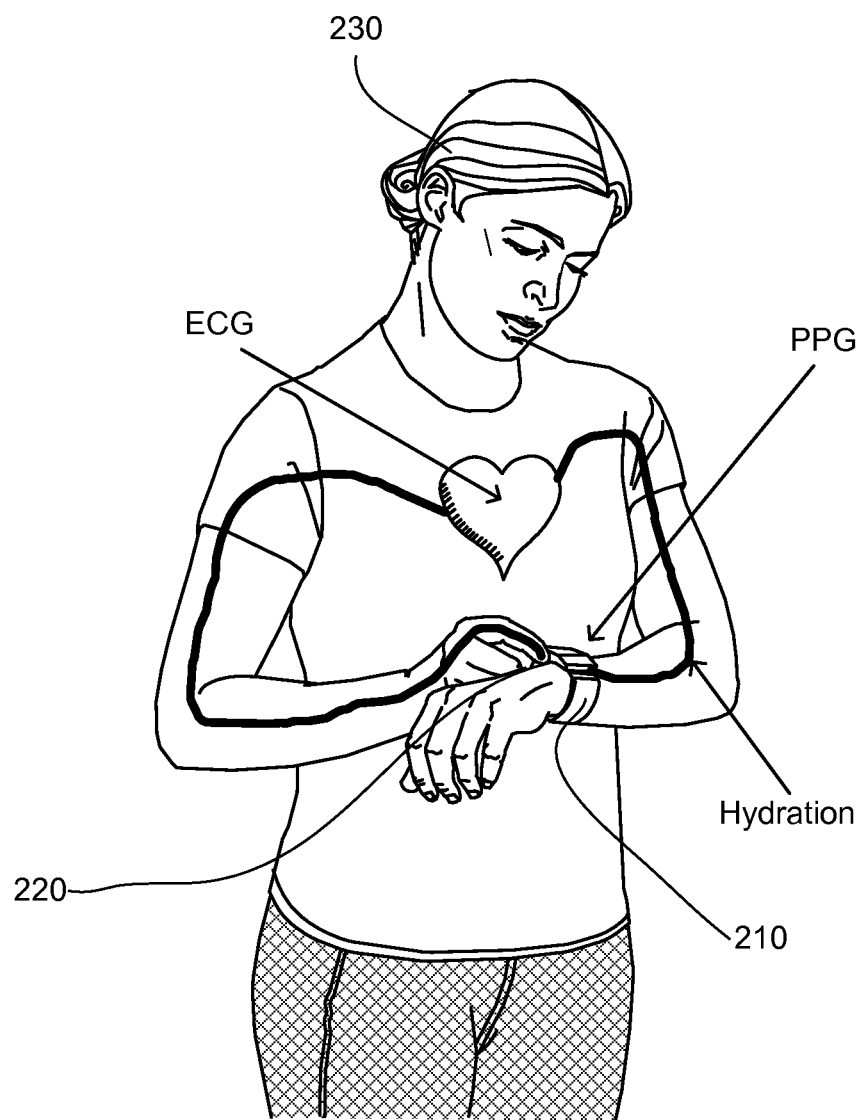
FIG. 2 illustrates a wristwatch device 310 configured to obtain PPG, ECG, and impedance measurements of a user, according to some implementations.

FIG. 2 illustrates a mobile wrist device 210 configured to obtain PPG, ECG, and impedance measurements of a user, according to some implementations. The mobile wrist device 210 illustrated in FIG. 2 is just one example of a mobile device 100 that may incorporate one or more implementations. That is, the mobile wrist device 210 may obtain PPG and ECG measurements of the user 230 via a plurality of contacts. In some implementations, one or more contacts may be placed at the bottom of the mobile wrist device 210, where the contact makes a continuous contact with the user's 230 wrist while the user 230 wears the mobile wrist device 210. In other implementations, a front surface of the mobile wrist device 210 may include a contact layer including, e.g., silver metal or Indium Tin Oxide (ITO). The mobile wrist device 210 may obtain both PPG and ECG measurements of the user 230. In some implementations, the front surface may be a touchscreen.

The mobile wrist device 210 may also include a button 220, which may be used to obtain a bodily function measurement. Alternatively, the button 220 may perform several functions, such as user input, and will be named "multifunction button 220" throughout the specification. Although named a "multifunction" button, it does not necessarily need to perform multiple functions. For example, the multifunction button 220 may be used by the user 230 to set a date and/or time for the mobile wrist device 210. The multifunction button 220 may have an integrated electrode on the surface. The user 230 may also use the multifunction button 220 to obtain an ECG measurement by touching the multifunction button 220 to complete a circuit (via the other contacts) through the user's 230 body. For example, another contact may be located on the bottom side of the wristwatch device's 210 face such that it is continuously in contact with the upper side of the user's 230 wrist. In some implementations, the multifunction button 220 may be integrated into a touchscreen of the mobile wrist device 210. The mobile wrist device 210 may then measure an electrical potential through the completed circuit to determine the ECG measurement.

The mobile wrist device 210 may also obtain a PPG measurement of the user 230 by using an optical based technology. For example, one or more light sources may be positioned at locations around the strap of the mobile wrist device 210. The light sources may shine light into the user's 230 skin, measure the blood flow through the user's 230 capillaries and thus determine a heart rate (PPG) of the user. This process is described in further detail below.

By obtaining both the PPG and ECG measurements of the user 230, a PTT technique may be used to determine the user's blood pressure. The mobile wrist device 210 may then provide important information to the user 230, based on the determined blood pressure.

The mobile wrist device 210 may be designed to be portable such that the user may easily wear the device or carry it on his/her person. In some implementations, the mobile wrist device 210 may perform everyday functions other than obtaining PPG, ECG, and impedance measurements of the user. For example, the mobile wrist device 210 may provide the current time, a stopwatch function, a calendar function, communication functions, etc. The PPG, ECG, and impedance measurements functions may be available in addition to the other described functions on the mobile wrist device 210.

Simplified Wrist Model

Figure 3:
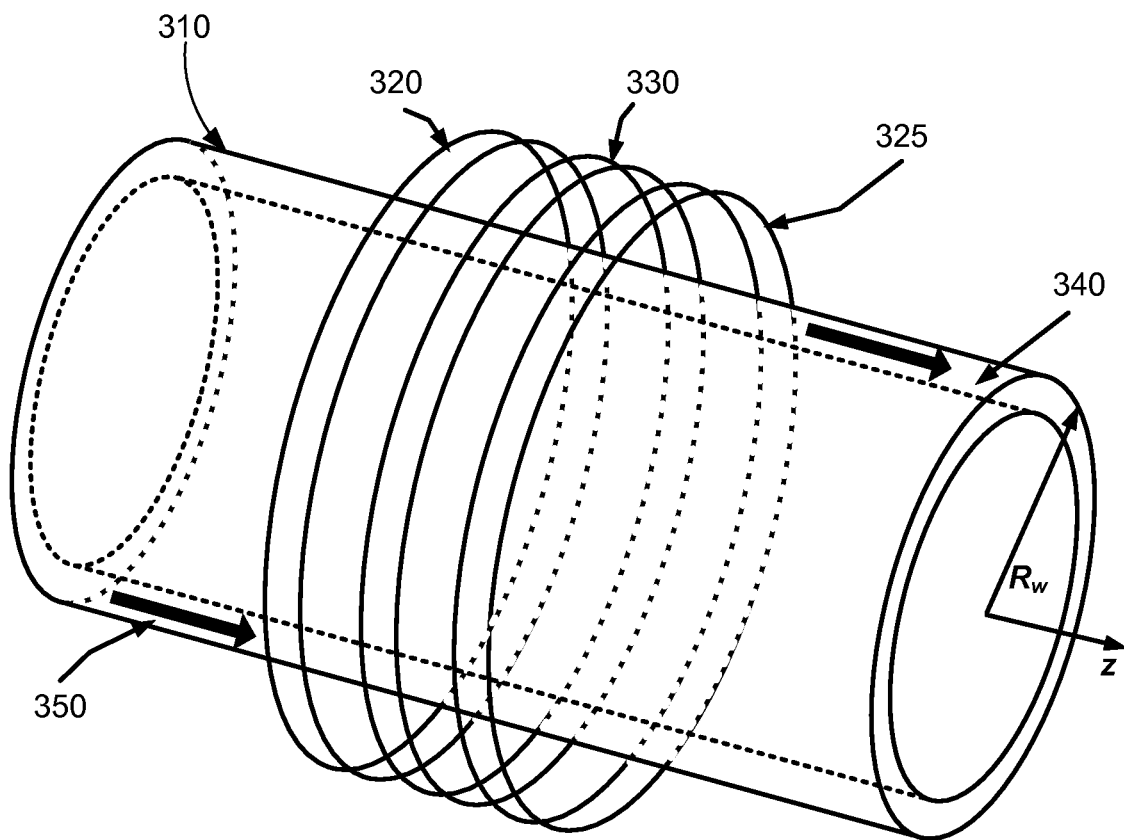
FIG. 3 illustrates a simplified wrist model 310, according to some implementations.

FIG. 3 illustrates a simplified wrist model 310, according to some implementations. The simplified wrist model 310 is discussed herein to explain the characteristics of light scattering in a user's wrist. The simplified wrist model 310 is represented by the cylindrical shape which can include tissue-like material perfused with blood-like liquid. The light emitting and light collecting portions of opto-electronics hardware of the PPG sensor are also shown in FIG. 3. The light emitting portion may include a central light emitting component 330 and the light collecting portions may include a left light collecting component 320 and a right light collecting component 325.

The simplified wrist model 310 may exemplify a user wrist by the cylindrical shape which may have a radius $R_W$ defining the wrist's curvature. This part may be composed of tissue-like scattering material that scatters light. Because both visible and near infrared (IR) light penetrates the tissue to a finite depth δ of several millimeters (e.g., tissue 340 has a thickness of δ), the simplified wrist model 310 may consider tissue that is only a few millimeters thick, which is light-accessible. The tissue 340 may be perfused with "blood-like" liquid to simulate a user's blood. Several larger and smaller artery-like vessels may also be present in the tissue 340 layer.

The simplified wrist model 310 may include a narrow cylindrical light source (e.g., light emitting component 330) that completely encompasses the circumference of the cylindrical shape exemplifying the wrist. The light emitting component 330 may direct substantially collimated light toward the center of the circumference in the form of a narrow sheet of light towards the wrist. The emitted light (e.g., incident light) may be partially reflected from the skin surface while also partially penetrating into the tissue to depth δ. During the process of the emitted light propagating in the tissue, the photons may experience multiple scattering events and very quickly the emitted light may turn into diffused light. Some of the light may be scattered back from the tissue. The scattered light may be reflected in a direction away from the wrist and may be captured by the light collecting components (e.g., left light collecting component 320 and right light collecting component 325). The light collecting components may capture the scattered light directed to them in a substantially small angular aperture.

Figure 4:
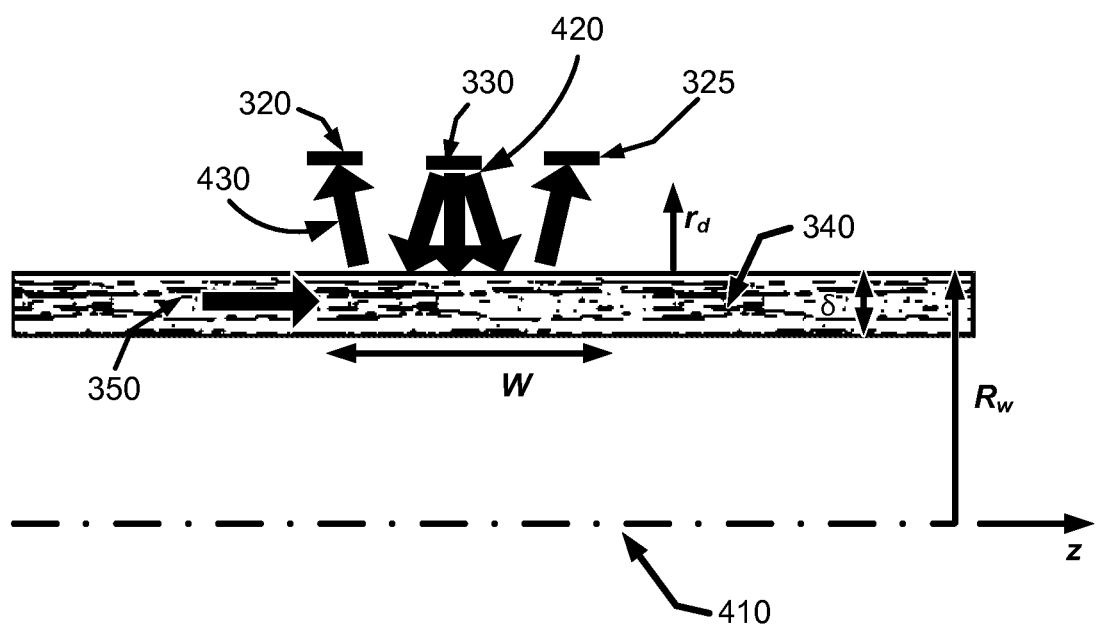
FIG. 4 illustrates a representation of the longitudinal cross-section of the simplified wrist model 310 depicted in FIG. 3, according to some implementations.

FIG. 4 illustrates a representation of the longitudinal cross-section of the simplified wrist model 310 depicted in FIG. 3, according to some implementations. The longitudinal cross-section is shown along a cylindrical axis 410. As described above, the simplified wrist model 310 may have a radius $R_W$ defining the wrist's curvature. Additionally, tissue 340 may have a thickness of δ. The optical components may have radii ($R_W+r_d$) enabling the PPG sensing features. Further, the light may be collected from the region shown having a characteristic length of W. In some implementations, W may be approximately 10 mm in length.

As described above, the light emitting component 330 may direct substantially collimated light toward the center of the circumference in the form of a narrow sheet of light towards the wrist. The emitted light 420 (e.g., incident light) may be partially reflected from the skin surface while also partially penetrating into the tissue to depth δ. During the process of the emitted light propagating in the tissue, the photons may experience multiple scattering events and very quickly the emitted light may turn into diffused light. Some of the light may be scattered back from the tissue (e.g., reflected light 430). The scattered light may be reflected in a direction away from the wrist and may be captured by the light collecting components (e.g., left light collecting component 320 and right light collecting component 325).

Figure 5:
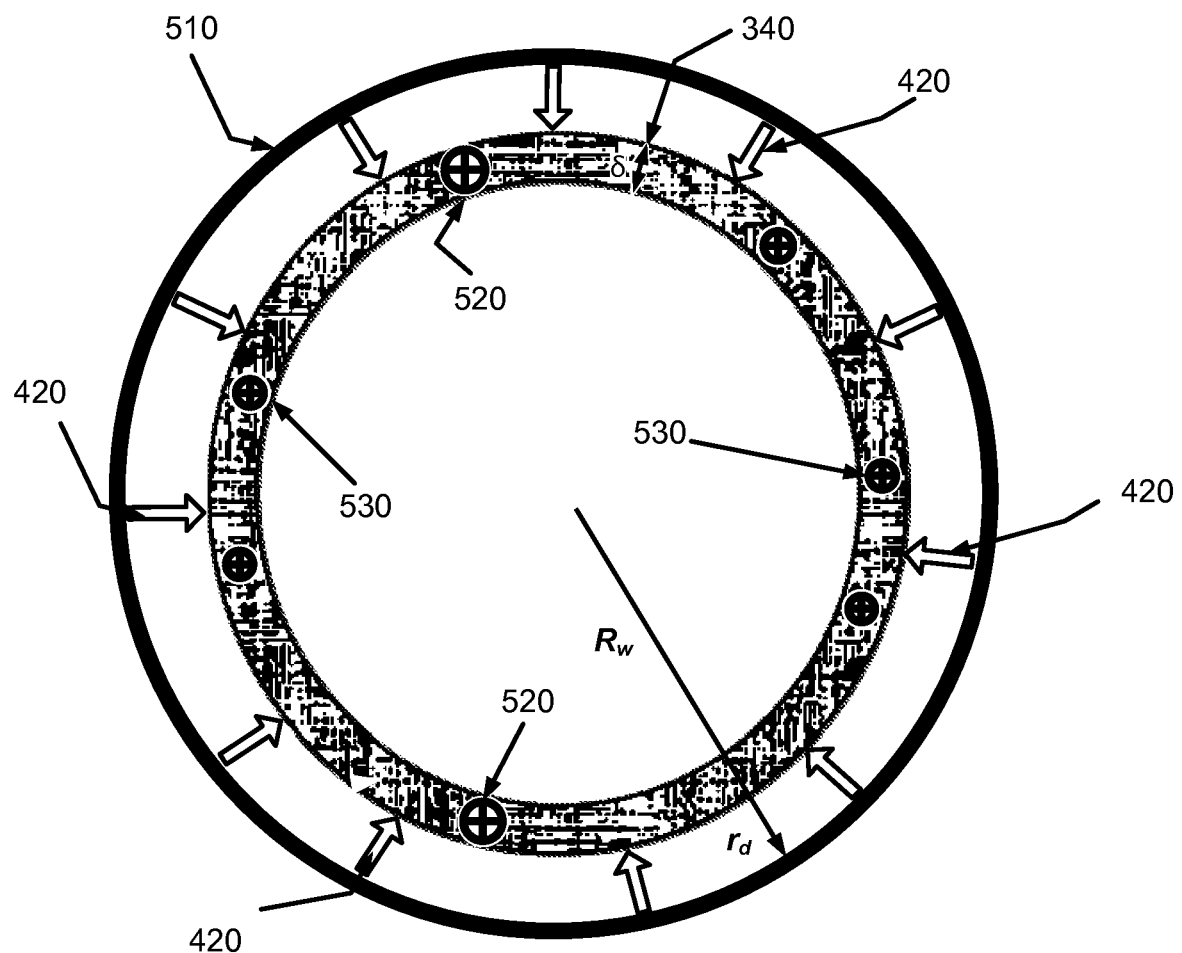
FIG. 5 illustrates a transversal cross-section of the simplified wrist model depicted in FIG. 3, according to some implementations.

FIG. 5 illustrates a transversal cross-section of the simplified wrist model 310 depicted in FIG. 3, according to some implementations. The figure shows a plurality of optical components 510 completely encompassing the wrist. The optical components 510 may include, for example, light emitting component 330, left light collecting component 320 and right light collecting component 325. The radius of the wrist is indicated by $R_W$ and the tissue 340 has a thickness of δ. Additionally, arteries 520 and arterioles 530 are shown which carry the blood along the transversal cross-section of the simplified wrist model.

The figure shows that if the optical components 510 were to move or rotate along the axis of the user's arm or finger, there would not be much of a change in the arteries 520 and arterioles 530 that would be probed by the emitted light 420 from the light emitting component 330. Since the arteries 520 and arterioles 530 run along the arm, they are not dipping into the region that the emitted light 420 cannot penetrate. Thus, as the optical components 510 rotate or otherwise move along the axis of the arm (e.g., where the longest arterial flow exists) or finger, the emitted light 420 may still directed toward a relatively constant cross section of arteries 520 and arterioles 530. By recognizing the symmetry of arterial blood flow, the arrangement of the optical components 510 encompassing the wrist allows for obtaining PPG measurements that are a lot less susceptible to motion artifacts than existing solutions allow for. It can be appreciated that the emitted light 420 may not need to be perfectly uniform, and only may need to be uniform enough such that the variation in light emission and collection is small with respect to the variation in the density of the arteries 520 and arterioles 530. In some implementations, the emitted light 420 by the light emitting component 330 may be green light which may penetrate further than other colored light.

It can be appreciated that while FIGS. 3-5 depict a simplified wrist model 310, the principles of the optical components encompassing the wrist can also be applied to other body parts where PPG measurements can be obtained (e.g., arm, finger, feet, legs, toes, etc.). Accordingly, the optical components could be implemented in a wrist-worn device such as a watch, a finger worn device such as a ring, or any other device.

The principles of the optical components 510 described above with respect to the simplified wrist model can further be described mathematically. Blood flux b, e.g. the amount of blood passing through the unit area of the transversal cross-section for the light-accessible tissue layer 340 of the wrist, may not be homogeneous. In other words, b may be a function of coordinates. Due to the cylindrical nature of the simplified wrist model, it may be convenient to use a cylindrical system of coordinates, therefore we can write:

$$=b(r,\vartheta,z) \quad \text{(Eq. 1)}$$

However, for a relatively small region of variation of longitudinal position of the particular cross-section $z_c$ the total amount of blood B in the light-accessible tissue layer 340 having length W may not be a function of coordinates, but rather may simply be a number, or a scalar:

$$B = W \cdot \oiint_A b(r, \theta, z)da \quad \text{(Eq. 2)}$$

Here, W may be a characteristic width of the PPG sensor along the z-dimension (e.g., along the arm) and A may be an area of the particular transversal cross-section of the wrist.

Referring back to FIG. 4 and following the same approach, we can derive that the total amount of reflected light $I_r$ collected by the PPG sensor, may again not be a function coordinates, but rather may simply be a number, or a scalar:

$$I_r \sim B(t) \cdot 2w \cdot (R_w + r_d) \cdot \oint_\theta i(r, \theta, z) d\theta = \qquad \text{(Eq. 3)}$$

$$4\pi \cdot k \cdot B(t) \cdot w \cdot (R_w + r_d) \cdot I_e$$

Here: B(t) may be an amount of blood accessible for probing by the PPG sensor calculated by Eq. 2; k may be a PPG coefficient that has many contributing values, including the efficiency of the photo sensor, source (e.g., LED) efficiency, optical properties of the combined sensor, etc.; w may be the width of one light collecting component of the PPG sensor along the z-dimension (e.g., typically between 1-3 mm); ($R_W$+$r_d$) may be the radius of the PPG sensor; i may be the density of light reflected by blood-perfused tissue; and $I_e$ may be the integral intensity of the light emitted by the PPG sensor.

It can be appreciated that in Eq. 3, B(t) is written as a function of time, and more specifically as a periodic function of time because blood is pumped by a beating heart.

Further, it can be appreciated that a conclusion to be drawn from Eq. 2 and Eq. 3 may be that if variations in radial and longitudinal positioning of the PPG sensor are small, the total amount of light collected by the sensor with the proposed geometry may be constant (e.g., independent of motion in either the longitudinal or radial directions). While the idealized cylindrical model is presented with respect to the simplified wrist model 310, the general principle expressed by the equations may hold true even for a traditional human wrist (or other body part) where the wrist may not adhere to the strict axi-symmetrical configuration illustrated.

The various perspectives shown in FIGS. 3-5 share a common theme. That is, the PPG sensor encloses the quasi-axi-symmetrical body part, such as the wrist, finger, ankle, leg, etc. The PPG sensor is designed in such a way as to ensure that relative motion of the PPG sensor with respect to the quasi-axi-symmetrical body part is small, and the light collecting optical components collect almost all the light scattered from the tissue. Thus, some relative motion can exist between the quasi-axi-symmetrical body part and the PPG sensor without disqualifying the measurements for being inaccurate due to motion artifacts. The existing solutions are not immune to such types of relative motion.

Wrist Ring Mobile Device

Figure 6:
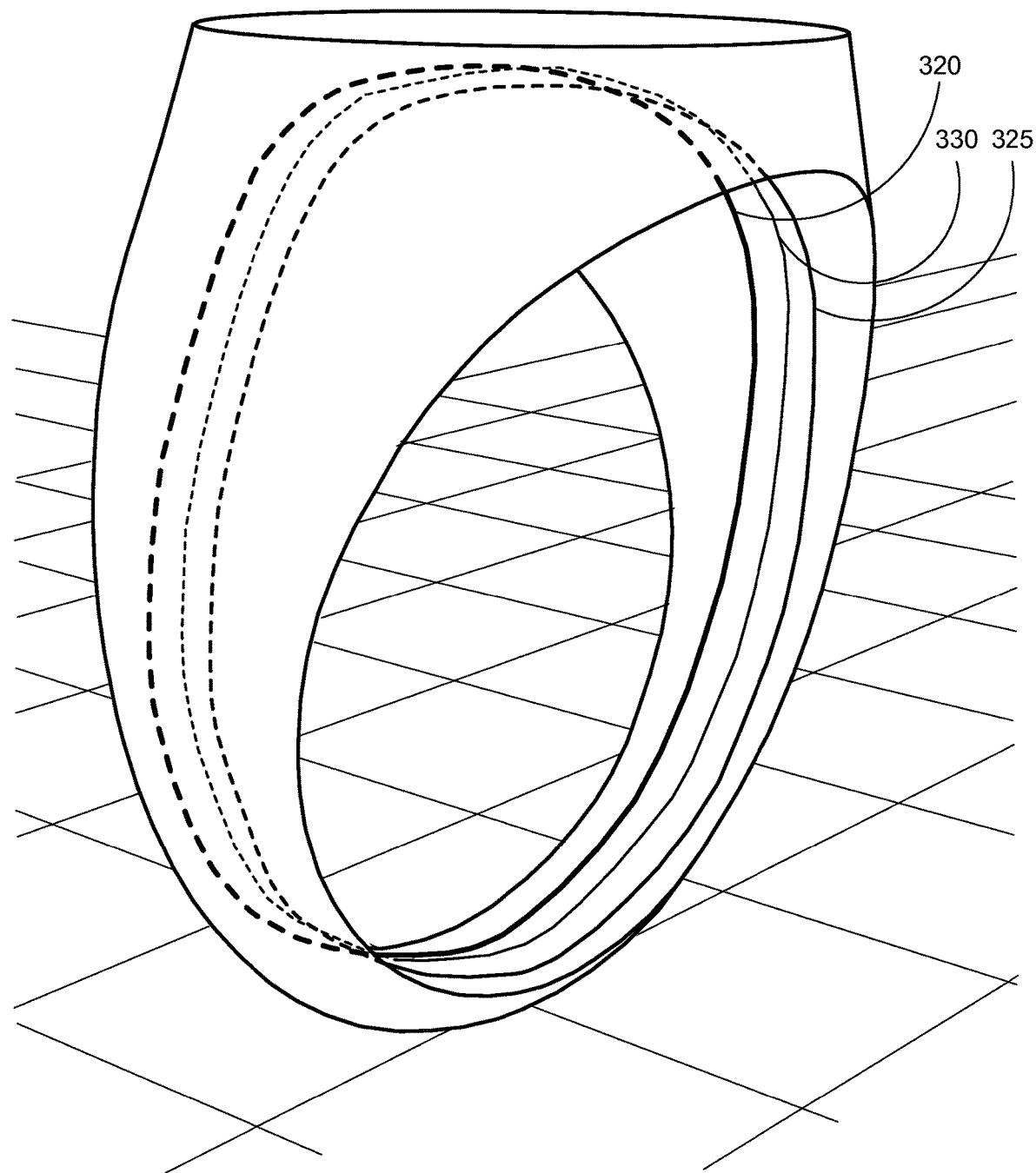
FIG. 6 illustrates a wrist ring including the described PPG sensor having a continuous light emitting component, according to some implementations.

FIG. 6 illustrates a wrist ring including the described PPG sensor having a continuous light emitting component, according to some implementations. The wrist ring may be an example of a mobile device 100. It can be appreciated that the wrist ring may be worn around any quasi-axi-symmetrical shape (e.g., wrist, finger, ankle, neck, etc.). The PPG sensor within the wrist wring may include light emitting component 330, left light collecting component 320 and right light collecting component 325. The implementation in FIG. 6 shows the light emitting component 330 as a continuous light source around the wrist ring. The continuous light source may be a ring of light within the wrist ring that extends along roughly the circumference of the wrist ring. When the wrist ring is worn by the user, the continuous light source may direct light into the user's tissue and the light collecting components 320 and 325 may detect the light reflected back to obtain a PPG measurement. It can be appreciated that while the wrist ring shows one light emitting component 330 and two light collecting components 320, 325, the PPG sensor in the wrist ring may contain any number of light emitting and light collecting components. In some implementations, the continuous light source may be implemented using a single light emitting component together with a light guide (described in further detail below).

In some implementations, the wrist ring may not need to be a continuous closed circle around the user's wrist. For example, the wrist ring can be a non-rigid ring and may have an arc-shaped form factor (or multiple arcs) that can fit around the user's wrist (or finger or other body part).

Figure 7:
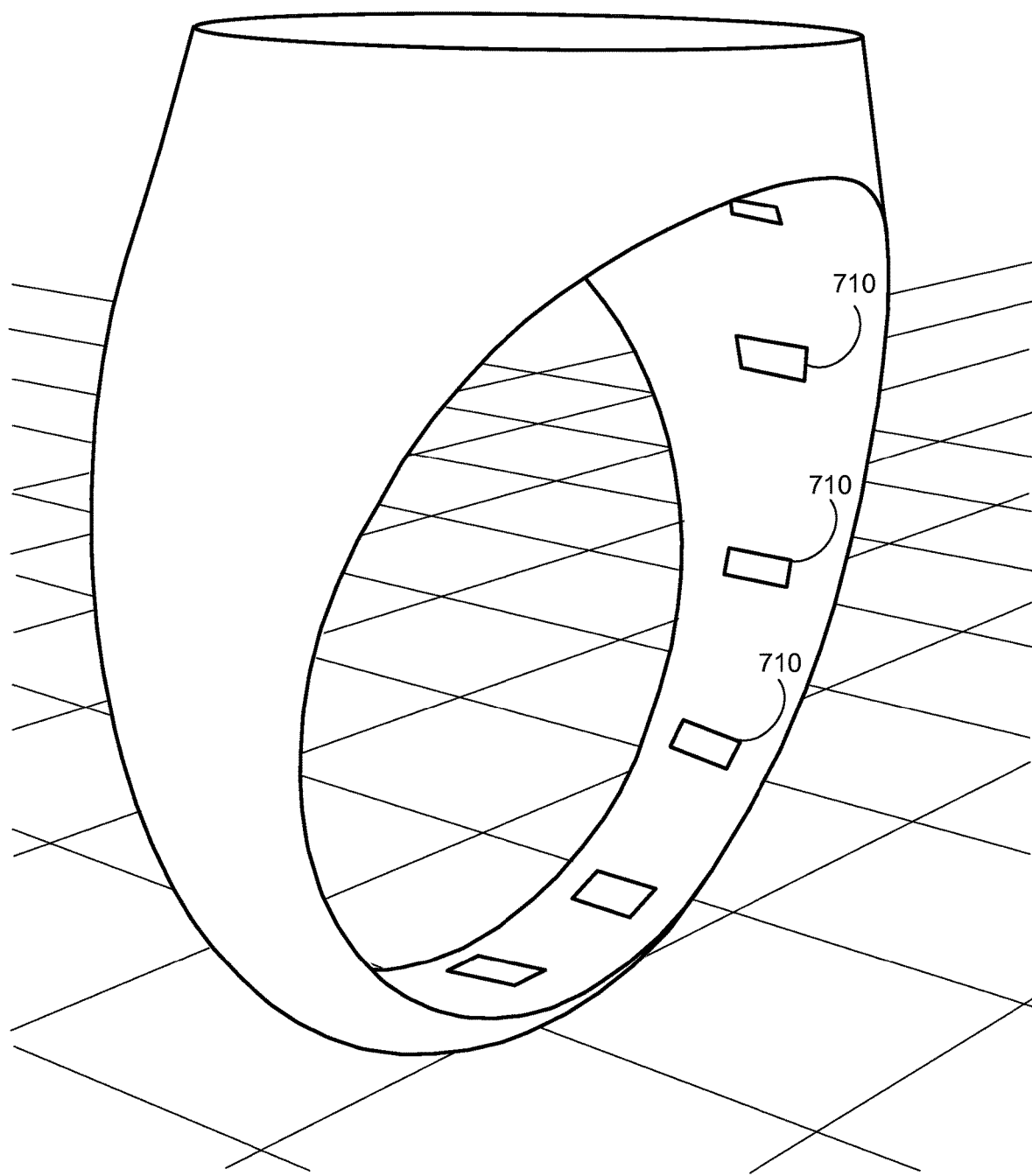
FIG. 7 illustrates a wrist ring including the described PPG sensor having discrete components, according to some implementations.

FIG. 7 illustrates a wrist ring including the described PPG sensor having discrete components, according to some implementations. The PPG sensor shown here may be composed of a plurality of discrete PPG sensors 710. Each discrete PPG sensor 710 may be spaced uniformly around the inner circumference of the wrist ring (e.g., 6 millimeters apart). The discrete PPG sensors 710 may be embedded into the inner surface of the wrist ring and spaced closely enough such that they are effectively a uniform light source. Each individual discrete PPG sensor 710 may include its own light emitting component and light collecting component(s) for detecting reflected light emitted by the light emitting component. While the PPG sensor is composed of discrete components, the implementation may obtain similar PPG measurements as obtained by the implementation in FIG. 6 which comprises a continuous light source. This may be due to the reasoning that this implementation may be viewed as a finite sum of the total collection signal in Eq. 3 above. More specifically, in the limit of a large number of discrete sensors, the sum would converge to the integral written in Eq. 3.

In some implementations, in order to obtain a PPG measurement, the measured reflected light by each of the light collecting components may first be averaged and the averaged value may then be used in the PPG measurement determination. In some implementations, another algorithm may be performed on the measured reflected light by each of the light collecting components prior to obtaining the PPG measurement.

Figure 8:
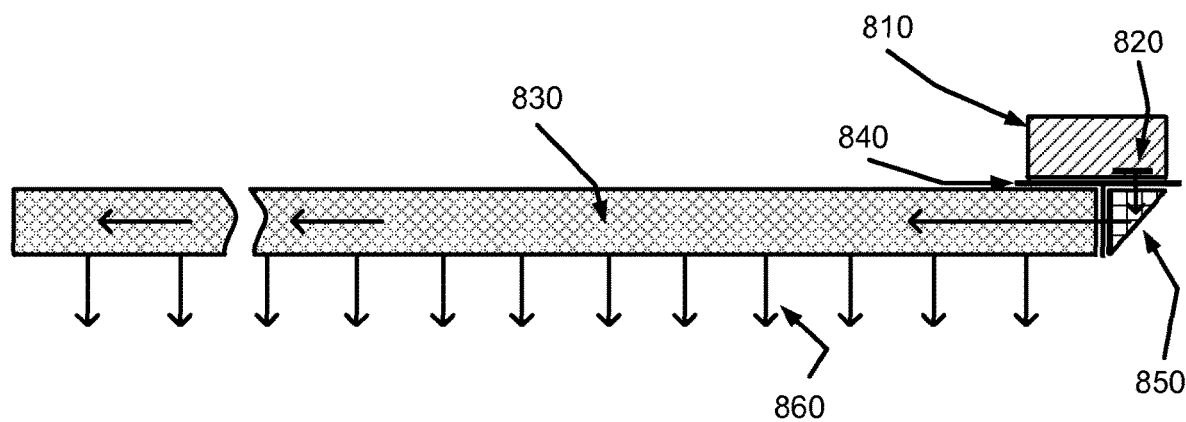
FIG. 8 illustrates a light emitting component together with a light guide, according to some implementations.

FIG. 8 illustrates a light emitting component together with a light guide, according to some implementations. As mentioned above, the "continuous" light source described with respect to FIG. 6 may be implemented using a single light emitting component 820 together with a light guide 830. The implementation shown in FIG. 8 includes a light emitting component 820 within a PPG sensor 810. The PPG sensor 810 may be attached to the light guide 830 and a 45 degree corner prism 850 by a layer of glue 840. While depicted here as straight in a cross-sectional representation, in practice the light guide 830 may actually wrap around and encompass the entire wrist (or other body part) of the user. When the light emitting component 820 emits light, the 45 degree corner prism 850 may direct the light into the light guide and the light guide may "turn" the light toward the skin of the user. The turned light 860 may enter the user's skin and reflect off of the user's tissue.

The main optics processing element for coupling the emitted light out to the user skin and for efficiently collecting the reflected light to the PPG sensor array may be a "turning film." The turning film design may incorporate two sets of linear facets: one for emitting light out of the light guide 830 and the other for collecting light into the light guide 830. The facets that turn light out of the light guide 830 may be positioned orthogonally to the collecting facets. Both sets of facets may be fabricated into the same surface of a plastic film. The facets may turn the light propagating into the film and make it leave the film and propagate normally to the film.

The light guide may allow for the use of a single (or just a few) light emitting components to emit light uniformly around the user's wrist (or other body part).

Figure 9:
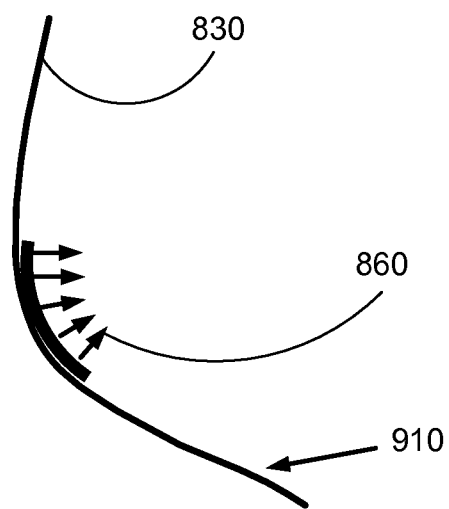
FIG. 9 illustrates a bendable light guide, according to some implementations.

FIG. 9 illustrates a bendable light guide, according to some implementations. The figure shows the light guide 830 in a bended fashion with an elastic band or adhesive patch as the carrier substrate 910. As can be seen, the turned light 860 may be directed in a direction away from the bend. For example, if the bended light guide encompassed a user's wrist, the turned light 860 may be directed uniformly around the circumference of the user's entire wrist.

The light collecting components may be coupled to adjacent features of the light guide. In some implementations, the width of the light guide comprising a light emitting component and two side light collecting components may be around 10-20 mm.

Figure 10A:
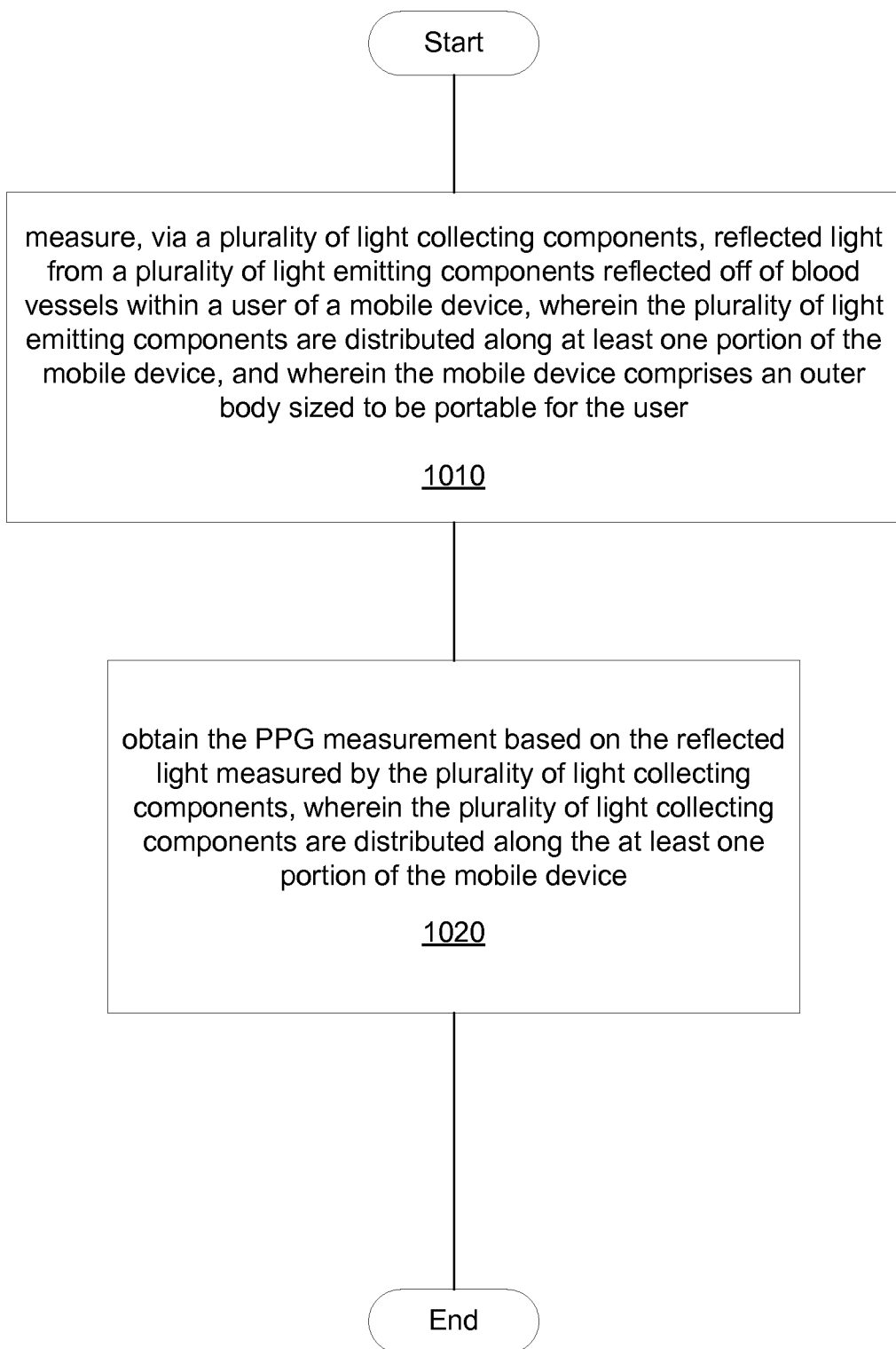
FIG. 10A is a flowchart of a method for obtaining a PPG measurement, according to some implementations.

FIG. 10A is a flowchart of a method for obtaining a PPG measurement using a plurality of discrete light emitting components, according to some implementations. In block 1010, reflected light from a plurality of light emitting components reflected off of blood vessels within a user of a mobile device is measured. The reflected light may be measured via a plurality of light collecting components. In some implementations, the light emitting components include LED light sources. In some implementations, the light collecting components include photodiodes. The light emitting components may be distributed along at least one portion of the mobile device. For example, in FIG. 7, the light emitting components are distributed along the 360 degree circumference of an inner portion of the wrist ring. In some implementations, the inner portion of the wrist ring may be less than 360 degrees in circumference (e.g., a wrist device that only encompasses a ¾ portion of the wrist). In some implementations, there may be at least three light emitting components distributed along the at least one portion of the mobile device. Further, the light emitting components may be distributed in an axially symmetrical fashion.

In block 1020, a PPG measurement is obtained based on the reflected light measured by the plurality of light collecting components. The plurality of light collecting components may also be distrusted along the at least one portion of the mobile device. In some implementations, the plurality of light collecting components may include photodiodes. The photodiodes may be positioned near the light emitting components (e.g., LED light sources). In some implementations, obtaining the PPG measurement may include averaging the measured reflected light by each of the light collecting components. In some implementations, a blood pressure measurement may be determined based on the obtained PPG measurement. For example, using pulse transit time techniques together with measured PPG and ECG data, a blood pressure measurement may be determined.

Figure 10B:
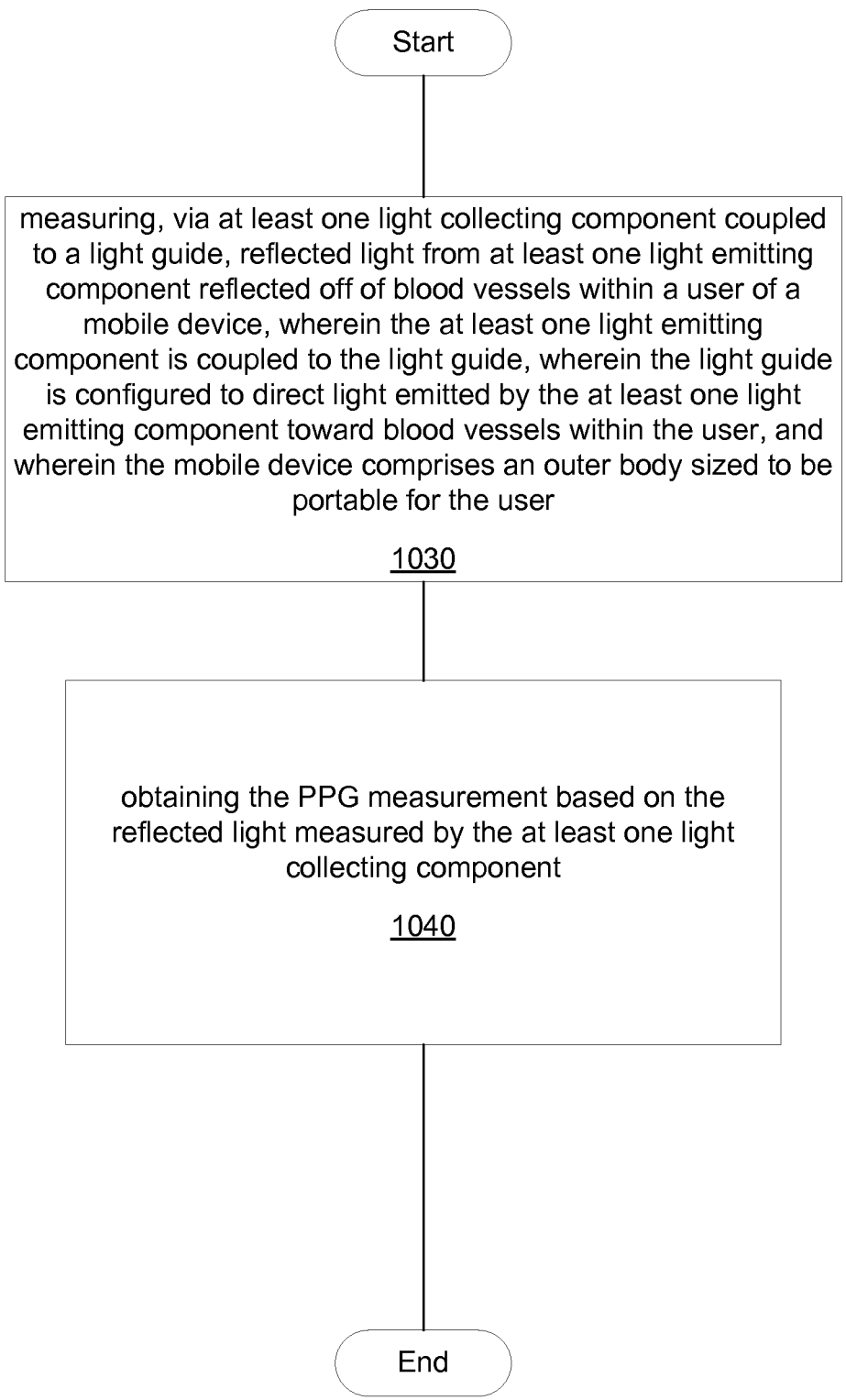
FIG. 10B is a flowchart of a method for obtaining a PPG measurement, using a continuous light emitting component, according to some implementations.

FIG. 10B is a flowchart of a method for obtaining a PPG measurement, using a continuous light emitting component, according to some implementations. In block 1030, reflected light from at least one light emitting component reflected off of blood vessels within a user of a mobile device is measured. The at least one light emitting component may include a LED light source. The light emitting component and at least one light collecting component may be coupled to a light guide. The light guide may include a turning film that is configured to direct light in a certain direction (e.g., towards blood vessels inside the user's body). For example, in FIG. 8, the light emitting component is glued to the light guide and the light guide directs the light down toward the user's body. Additionally, the mobile device may have an outer body that is sized to be portable for the user. The outer body may have a 360 degree circumference and the light guide may encompass the 360 degree circumference, as shown in FIG. 6.

In block 1040, a PPG measurement based on the reflected light measured by the at least one light collecting component is obtained. In some implementations, a blood pressure measurement may be determined based on the obtained PPG measurement. For example, using pulse transit time techniques together with measured PPG and ECG data, a blood pressure measurement may be determined.

Figure 11:
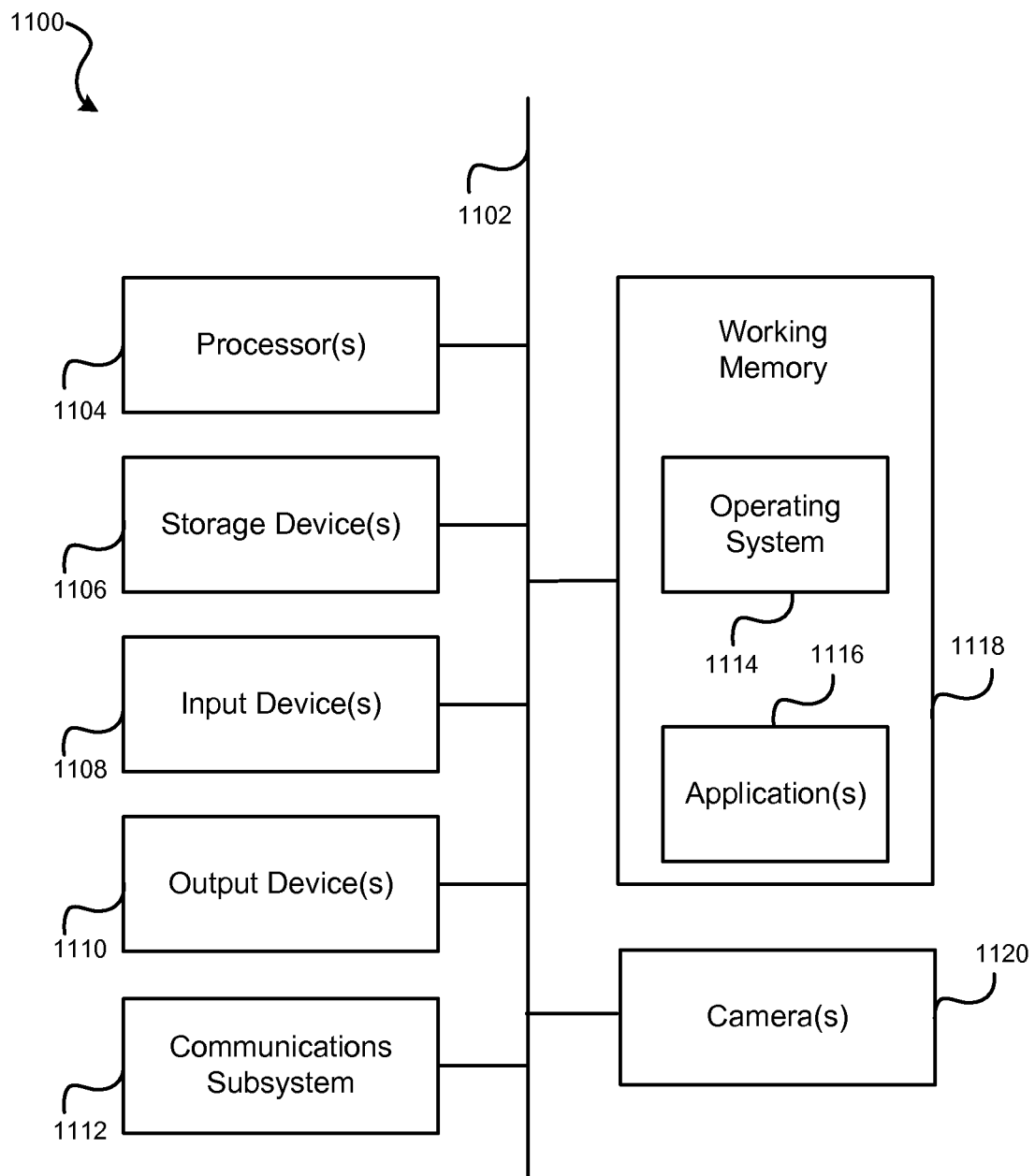
FIG. 11 illustrates an example of a computing system in which one or more embodiments may be implemented.

FIG. 11 illustrates an example of a computing system in which one or more embodiments may be implemented. A computer system as illustrated in FIG. 11 may be incorporated as part of the above described computerized device. For example, computer system 1100 can represent some of the components of a television, a computing device, a server, a desktop, a workstation, a control or interaction system in an automobile, a tablet, a netbook or any other suitable computing system. A computing device may be any computing device with an image capture device or input sensory unit and a user output device. An image capture device or input sensory unit may be a camera device. A user output device may be a display unit. Examples of a computing device include but are not limited to video game consoles, tablets, smart phones and any other hand-held devices. FIG. 11 provides a schematic illustration of one embodiment of a computer system 1100 that can perform the methods provided by various other embodiments, as described herein, and/or can function as the host computer system, a remote kiosk/terminal, a point-of-sale device, a telephonic or navigation or multimedia interface in an automobile, a computing device, a set-top box, a table computer and/or a computer system. FIG. 11 is meant only to provide a generalized illustration of various components, any or all of which may be utilized as appropriate. FIG. 11, therefore, broadly illustrates how individual system elements may be implemented in a relatively separated or relatively more integrated manner. In some embodiments, elements of computer system 1100 may be used to implement functionality of the mobile device 100 in FIG. 1.

The computer system 1100 is shown comprising hardware elements that can be electrically coupled via a bus 1102 (or may otherwise be in communication, as appropriate). The hardware elements may include one or more processors 1104, including without limitation one or more general-purpose processors and/or one or more special-purpose processors (such as digital signal processing chips, graphics acceleration processors, and/or the like); one or more input devices 1108, which can include without limitation one or more cameras, sensors, a mouse, a keyboard, a microphone configured to detect ultrasound or other sounds, and/or the like; and one or more output devices 1110, which can include without limitation a display unit such as the device used in some implementations, a printer and/or the like.

In some implementations, various input devices 1108 and output devices 1110 may be embedded into interfaces such as display devices, tables, floors, walls, and window screens. Furthermore, input devices 1108 and output devices 1110 coupled to the processors may form multi-dimensional tracking systems.

The computer system 1100 may further include (and/or be in communication with) one or more non-transitory storage devices 1106, which can comprise, without limitation, local and/or network accessible storage, and/or can include, without limitation, a disk drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data storage, including without limitation, various file systems, database structures, and/or the like.

The computer system 1100 might also include a communications subsystem 1112, which can include without limitation a modem, a network card (wireless or wired), an infrared communication device, a wireless communication device and/or chipset (such as a Bluetooth™ device, an 802.11 device, a Wi-Fi device, a WiMax device, cellular communication facilities, etc.), and/or the like. The communications subsystem 1112 may permit data to be exchanged with a network, other computer systems, and/or any other devices described herein. In many embodiments, the computer system 1100 will further comprise a nontransitory working memory 1118, which can include a RAM or ROM device, as described above.

The computer system 1100 also can comprise software elements, shown as being currently located within the working memory 1118, including an operating system 1114, device drivers, executable libraries, and/or other code, such as one or more application programs 1116, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a computer-readable storage medium, such as the storage device(s) 1106 described above. In some cases, the storage medium might be incorporated within a computer system, such as computer system 1100. In other embodiments, the storage medium might be separate from a computer system (e.g., a removable medium, such as a compact disc), and/or provided in an installation package, such that the storage medium can be used to program, configure and/or adapt a general purpose computer with the instructions/code stored thereon. These instructions might take the form of executable code, which is executable by the computer system 1100 and/or might take the form of source and/or installable code, which, upon compilation and/or installation on the computer system 1100 (e.g., using any of a variety of generally available compilers, installation programs, compression/decompression utilities, etc.) then takes the form of executable code.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed. In some embodiments, one or more elements of the computer system 1100 may be omitted or may be implemented separate from the illustrated system. For example, the processor 1104 and/or other elements may be implemented separate from the input device 1108. In one embodiment, the processor is configured to receive images from one or more cameras that are separately implemented.

In some embodiments, elements in addition to those illustrated in FIG. 11 may be included in the computer system 1100.

Some embodiments may employ a computer system (such as the computer system 1100) to perform methods in accordance with the disclosure. For example, some or all of the procedures of the described methods may be performed by the computer system 1100 in response to processor 1104 executing one or more sequences of one or more instructions (which might be incorporated into the operating system 1114 and/or other code, such as an application program 1116) contained in the working memory 1118. Such instructions may be read into the working memory 1118 from another computer-readable medium, such as one or more of the storage device(s) 1106. Merely by way of example, execution of the sequences of instructions contained in the working memory 1118 might cause the processor(s) 1104 to perform one or more procedures of the methods described herein.

The terms "machine-readable medium" and "computer-readable medium," as used herein, refer to any medium that participates in providing data that causes a machine to operate in a specific fashion. In some embodiments implemented using the computer system 1100, various computer-readable media might be involved in providing instructions/code to processor(s) 1104 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media include, for example, optical and/or magnetic disks, such as the storage device(s) 1106. Volatile media include, without limitation, dynamic memory, such as the working memory 1118. Transmission media include, without limitation, coaxial cables, copper wire and fiber optics, including the wires that comprise the bus 1102, as well as the various components of the communications subsystem 1112 (and/or the media by which the communications subsystem 1112 provides communication with other devices). Hence, transmission media can also take the form of waves (including without limitation radio, acoustic and/or light waves, such as those generated during radio-wave and infrared data communications).

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of computer-readable media may be involved in carrying one or more sequences of one or more instructions to the processor(s) 1004 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 1100. These signals, which might be in the form of electromagnetic signals, acoustic signals, optical signals and/or the like, are all examples of carrier waves on which instructions can be encoded, in accordance with various implementations.

The communications subsystem 1112 (and/or components thereof) generally will receive the signals, and the bus 1102 then might carry the signals (and/or the data, instructions, etc. carried by the signals) to the working memory 1118, from which the processor(s) 1104 retrieves and executes the instructions. The instructions received by the working memory 1118 may optionally be stored on a non-transitory storage device 1106 either before or after execution by the processor(s) 1104.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the implementations described herein. Also, a number of steps may be undertaken before, during, or after the above elements are considered.

What is claimed is:

1. A mobile device for obtaining a photoplethysmography (PPG) measurement, comprising:
    an outer body sized to be portable for a user of the mobile device;
    at least one light emitting component located along at least one portion of the mobile device;
    a turning film comprising a first set of facets and a second set of facets separate from the first set of facets, wherein the first set of facets is configured to direct light emitted from the at least one light emitting component, the emitted light being propagated into the turning film and directed through a surface of the turning film, along a direction perpendicular to the surface of the turning film toward blood vessels within the user, and wherein the second set of facets is configured to collect reflected light, the reflected light being received at the surface of the turning film and corresponding to the emitted light reflected off the blood vessels;
    a plurality of light collecting components configured to measure the reflected light collected by the turning film, wherein the plurality of light collecting components are distributed along the at least one portion of the mobile device, and wherein a processor is configured to obtain the PPG measurement based on the reflected light measured by the plurality of light collecting components.

2. The mobile device of claim 1, wherein the at least one portion is at least one of a 360 degree circumference or less than a 360 degree circumference.

3. The mobile device of claim 1, wherein the processor is further configured to average the reflected light measured by each of the plurality of light collecting components.

4. The mobile device of claim 1, wherein the at least one light emitting component includes a plurality of light emitting components distributed along the at least one portion of the mobile device in an axially symmetrical arrangement.

5. The mobile device of claim 1, wherein the processor is further configured to determine a blood pressure (BP) measurement of the user based at least in part on the obtained PPG measurement.

6. The mobile device of claim 1, wherein the mobile device is one of a watch, ring, or bracelet.

7. The mobile device of claim 1, wherein the at least one light emitting component comprises at least one light emitting diode, and the plurality of light collecting components comprise photodiodes.

8. The mobile device of claim 1, wherein facets of the first set of facets are positioned orthogonally to facets of the second set of facets.

9. A method for obtaining a photoplethysmography (PPG) measurement, comprising:
    measuring, via a plurality of light collecting components, reflected light collected by a turning film of a mobile device, the turning film comprising a first set of facets and a second set of facets separate from the first set of facets, wherein the first set of facets is configured to direct light emitted from at least one light emitting component located along at least one portion of the mobile device, the emitted light being propagated into the turning film and directed through a surface of the turning film, along a direction perpendicular to the surface of the turning film toward blood vessels within a user, wherein the second set of facets is configured to collect the reflected light, the reflected light being received at the surface of the turning film and corresponding to the emitted light reflected off the blood vessels, and wherein the mobile device comprises an outer body sized to be portable for the user; and
    obtaining the PPG measurement based on the reflected light measured by the plurality of light collecting components, wherein the plurality of light collecting components are distributed along the at least one portion of the mobile device.

10. The method of claim 9, wherein the at least one portion is a 360 degree circumference.

11. The method of claim 9, further comprising averaging the reflected light measured by each of the plurality of light collecting components.

12. The method of claim 9, wherein the at least one light emitting component includes a plurality of light emitting components distributed along the at least one portion of the mobile device in an axially symmetrical arrangement.

13. The method of claim 9, further comprising determining a blood pressure (BP) measurement of the user based at least in part on the obtained PPG measurement.

14. The method of claim 9, wherein the mobile device is one of a watch, ring, or bracelet.

15. The method of claim 9, wherein the at least one light emitting component comprises at least one light emitting diode, and the plurality of light collecting components comprise photodiodes.

16. The method of claim 9, wherein facets of the first set of facets are positioned orthogonally to facets of the second set of facets.

17. An apparatus for obtaining a photoplethysmography (PPG) measurement, comprising:
means for measuring, via a plurality of light collecting components, reflected light collected by a turning film of a mobile device, the turning film comprising a first set of facets and a second set of facets separate from the first set of facets, wherein the first set of facets is configured to direct light emitted from at least one light emitting component located along at least one portion of the mobile device, the emitted light being propagated into the turning film and directed through a surface of the turning film, along a direction perpendicular to the surface of the turning film toward blood vessels within a user, wherein the second set of facets is configured to collect the reflected light, the reflected light being received at the surface of the turning film and corresponding to the emitted light reflected off the blood vessels, and wherein the mobile device comprises an outer body sized to be portable for the user; and
means for obtaining the PPG measurement based on the reflected light measured by the means for measuring, wherein the plurality of light collecting components are distributed along the at least one portion of the mobile device.

18. The apparatus of claim 17, wherein the at least one portion is a 360 degree circumference.

19. The apparatus of claim 17, further comprising means for averaging the reflected light measured by the means for measuring.

20. The apparatus of claim 17, wherein the at least one light emitting component includes a plurality of light emitting components distributed along the at least one portion of the mobile device in an axially symmetrical arrangement.

21. The apparatus of claim 17, further comprising means for determining a blood pressure (BP) measurement of the user based at least in part on the obtained PPG measurement.

22. The apparatus of claim 17, wherein the at least one light emitting component comprises at least one light emitting diode, and the plurality of light collecting components comprise photodiodes.

23. The apparatus of claim 17, wherein facets of the first set of facets are positioned orthogonally to facets of the second set of facets.

24. One or more non-transitory computer-readable media storing computer-executable instructions for obtaining a photoplethysmography (PPG) measurement, wherein the instructions, when executed, cause one or more computing devices included in a mobile device to:
measure, via a plurality of light collecting components, reflected light collected by a turning film of the mobile device, the turning film comprising a first set of facets and a second set of facets separate from the first set of facets, wherein the first set of facets is configured to direct light emitted from at least one light emitting component located along at least one portion of the mobile device, the emitted light being propagated into the turning film and directed through a surface of the turning film, along a direction perpendicular to the surface of the turning film toward blood vessels within a user, wherein the second set of facets is configured to collect the reflected light, the reflected light being received at the surface of the turning film and corresponding to the emitted light reflected off the blood vessels, and wherein the mobile device comprises an outer body sized to be portable for the user; and
obtain the PPG measurement based on the reflected light measured by the plurality of light collecting components, wherein the plurality of light collecting components are distributed along the at least one portion of the mobile device.

25. The non-transitory computer-readable media of claim 24, wherein the at least one portion is a 360 degree circumference.

26. The non-transitory computer-readable media of claim 24, wherein the instructions, when executed, further cause the one or more computing devices to average the reflected light measured by each of the plurality of light collecting components.

27. The non-transitory computer-readable media of claim 24, wherein the at least one light emitting component includes a plurality of light emitting components distributed along the at least one portion of the mobile device in an axially symmetrical arrangement.

28. The non-transitory computer-readable media of claim 24, wherein the instructions, when executed, further cause the one or more computing devices to determine a blood pressure (BP) measurement of the user based at least in part on the obtained PPG measurement.

29. The non-transitory computer-readable media of claim 24, wherein the at least one light emitting component comprises at least one light emitting diode, and the plurality of light collecting components comprise photodiodes.

30. The non-transitory computer-readable media of claim 24, wherein facets of the first set of facets are positioned orthogonally to facets of the second set of facets.

* * * * *